United States Patent [19]

Ryaby et al.

[11] 4,105,017

[45] Aug. 8, 1978

[54] MODIFICATION OF THE GROWTH REPAIR AND MAINTENANCE BEHAVIOR OF LIVING TISSUE AND CELLS BY A SPECIFIC AND SELECTIVE CHANGE IN ELECTRICAL ENVIRONMENT

[75] Inventors: John P. Ryaby, Essex Fells; Arthur A. Pilla, Wyckoff, both of N.J.

[73] Assignee: Electro-Biology, Inc., Fairfield, N.J.

[21] Appl. No.: 742,706

[22] Filed: Nov. 17, 1976

Related U.S. Application Data

[63] Continuation-in-part of Ser. No. 633,408, Nov. 19, 1975, abandoned.

[51] Int. Cl.² ................................................ A61N 1/40
[52] U.S. Cl. ................................. 128/1.5; 128/82.1; 128/419 F; 128/421
[58] Field of Search ........................ 128/1.3, 1.5, 82.1, 128/404, 413, 419 F, 419 R, 420 R, 421, 422, 423

[56] References Cited

U.S. PATENT DOCUMENTS

| | | | |
|---|---|---|---|
| 3,055,372 | 9/1962 | Browner | 128/421 |
| 3,566,877 | 3/1971 | Smith | 128/422 |
| 3,745,995 | 7/1973 | Kraus | 128/82.1 |
| 3,890,953 | 6/1975 | Kraus et al. | 128/1.5 |
| 3,893,462 | 7/1975 | Manning | 128/421 |
| 3,911,930 | 10/1975 | Hagfors et al. | 128/421 |
| 3,915,151 | 10/1975 | Kraus | 128/1.5 |
| 3,952,751 | 4/1976 | Yarger | 128/422 |

OTHER PUBLICATIONS

Bassett et al., "Augmentation of Bone Repair . . . EM Fields.", Science, vol. 184, pp. 575–577, May 1974.
Braden et al., "Electrical . . . Dental Hard Tissues", Nature, pp. 1565–1566, Dec. 1966.
Maass et al., "Contactless Nerve Stimulation . . . Transducer", IEEE Trans on Magnetics, vol. 6, No. 2, pp. 322–326, Jun. 1970.

*Primary Examiner*—Kyle L. Howell
*Assistant Examiner*—Lee S. Cohen
*Attorney, Agent, or Firm*—Hopgood, Calimafde, Kalil, Blaustein & Lieberman

[57] ABSTRACT

Surgically non-invasive method of and apparatus for altering the growth, repair of maintenance behavior of living tissues and/or cells by inducing voltage and concomitant current pulses of specific time-frequency - amplitude relations therewithin.

50 Claims, 8 Drawing Figures

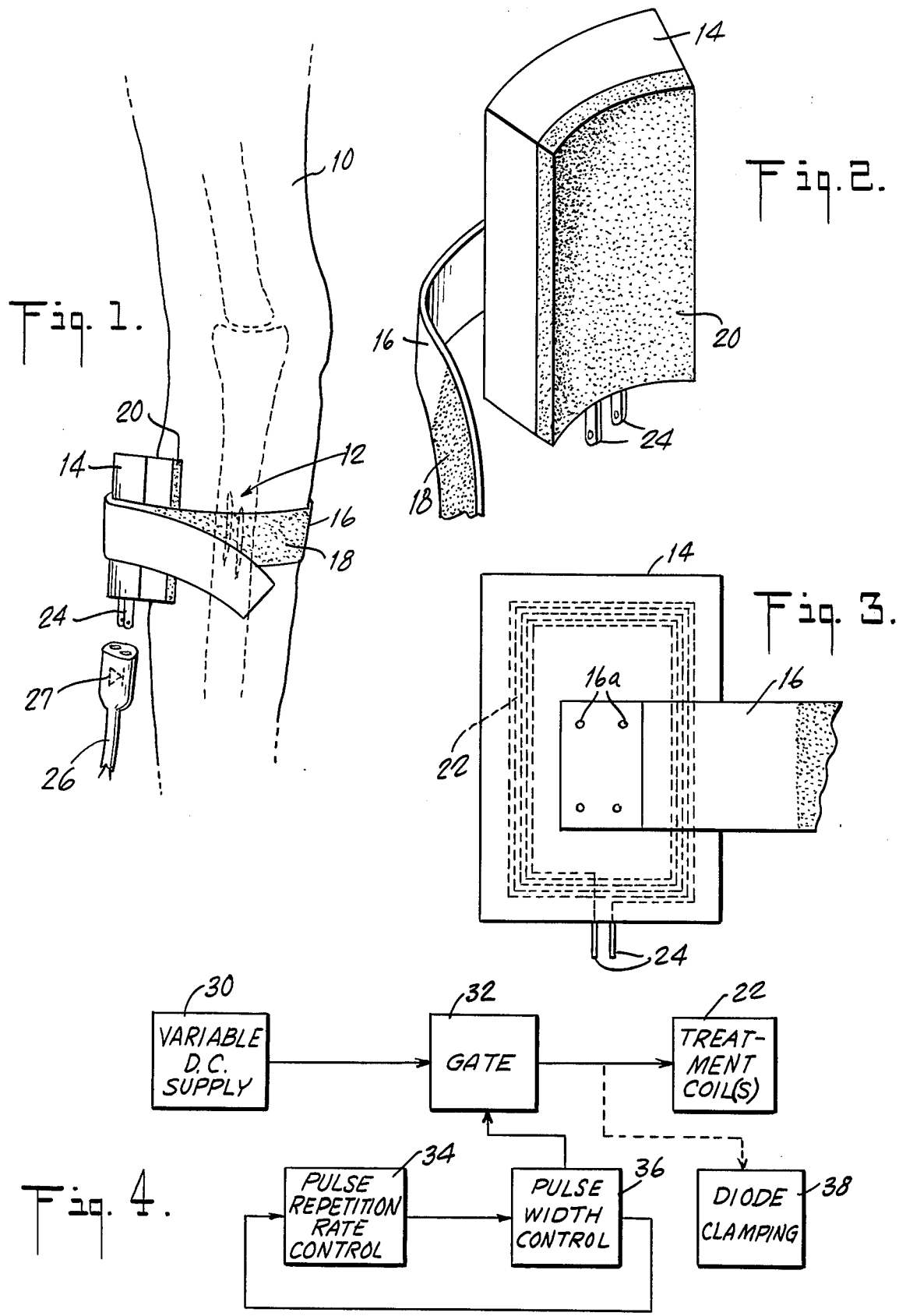

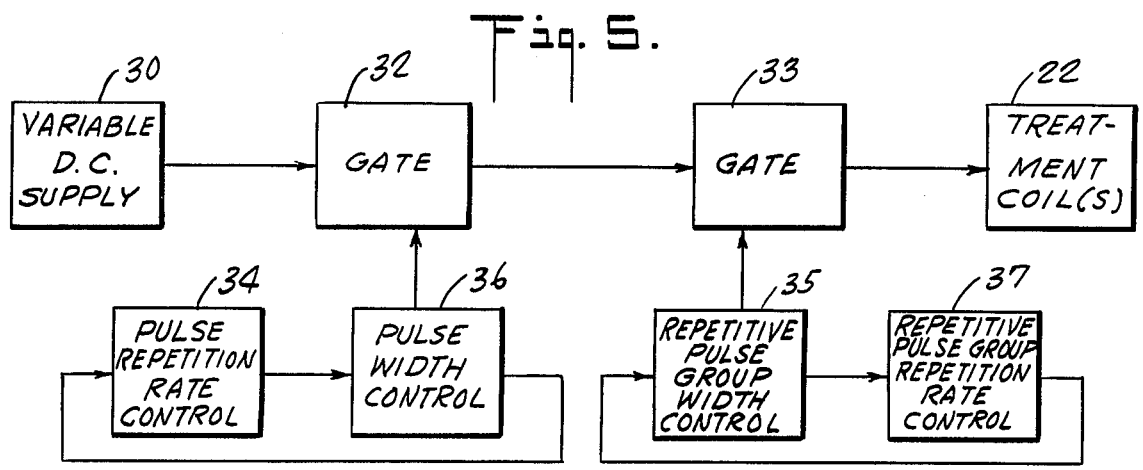
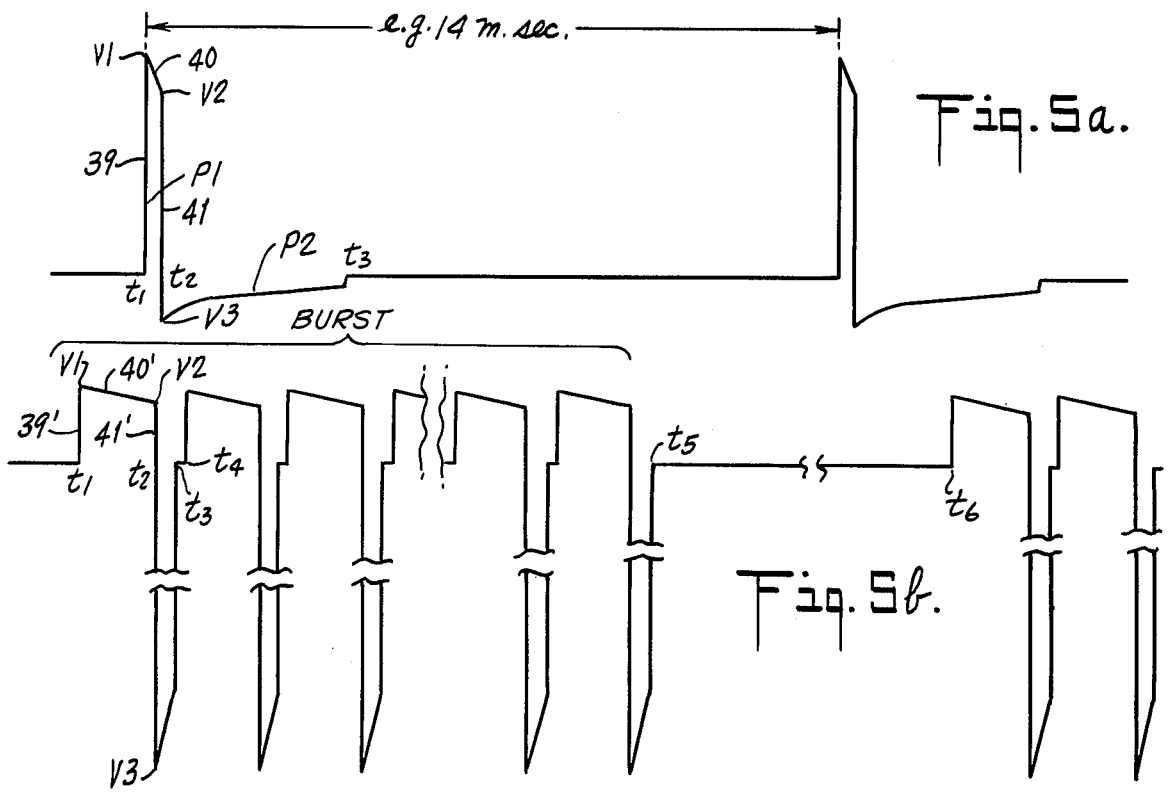
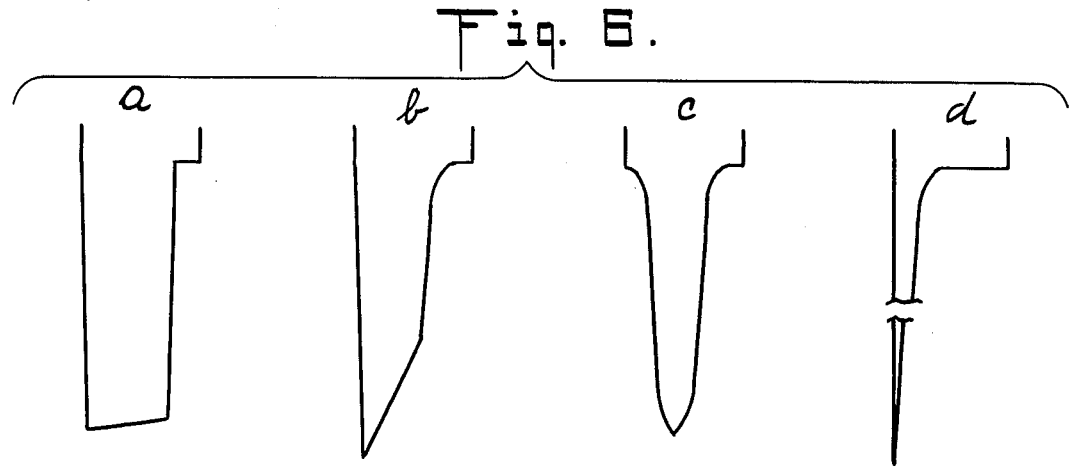

MODIFICATION OF THE GROWTH REPAIR AND MAINTENANCE BEHAVIOR OF LIVING TISSUE AND CELLS BY A SPECIFIC AND SELECTIVE CHANGE IN ELECTRICAL ENVIRONMENT

CROSS-REFERENCE

This application is a continuation-in-part application of Ser. No. 633,408 filed on Nov. 19, 1975, entitled "Modification of the Behavior of Living Tissue and Cells by Electrical Means", said Ser. No. 633,408 being now abandoned.

BACKGROUND AND BRIEF DESCRIPTION OF THE INVENTION

This invention relates to the treatment of living tissues and/or cells by altering their interaction with the charged species in their environment. In particular, the invention relates to a controlled modification of cellular and/or tissue growth, repair and maintenance behaviour by the application of encoded electrical information. Still more particularly, this invention provides for the application, by a surgically non-invasive direct inductive coupling, of one or more electrical voltage and concomitant current signals conforming to a highly specific pattern.

Several attempts have been made in the past to elicit a response of living tissue to electrical signals.

Investigations have been conducted involving the use of direct current, alternating current, and pulsed signals of single and double polarity. Invasive treatments involving the use of implanted electrodes have been followed, as well as non-invasive techniques utilizing electrostatic and electromagnetic fields. Much of the prior work that has been done is described in Volume 238 of the *Annals of the New York Academy of Sciences* published Oct. 11, 1974 and entitled "Electrically Mediated Growth Mechanisms in Living Systems" (Editors A. R. Liboff and R. A. Rinaldi). See also "Augmentation of Bone Repair by Inductively Coupled Electromagnetic Fields" by C. Andrew L. Bassett, Robert J. Pawluk and Arther A. Pilla published in Volume 184, pages 575–577 of *Science* (May 3, 1974).

The invention herein is based upon basic cellular studies and analyses which involve a detailed consideration of the interactions of charged species, such as divalent cations and hormones at a cell's interfaces and junctions.

Basically it has been established that, by changing the electrical and/or electrochemical environment of a living cell and/or tissue, a modification, often a beneficial therapeutic effect, of the growth, repair and maintenance behavior of said tissue and/or cells can be achieved. This modification or effect is carried out by subjecting the desired area of tissues and/or cells to a specifically encoded electrical voltage and concomitant current, whereby the interactions of charged species at the cells' surfaces are modified. Such modifications engender a change in the state or function of the cell or tissue which may result in a beneficial influence on the treated site. For example, in the specific case of bone growth and repair, it is possible with one electrical code, hereinafter referred to as Mode 1, to change the interaction of the ion such as $Ca^{2+}$ with a cell's membranes. Whereas, with another electrical code, hereinafter referred to as Mode 2, a modification in the same cell's protein synthesis capabilities can be affected.

For example, tissue culture experiments involving the study of embryonic chick limb rudiments show that the use of a Mode 1 code signal elicits enhanced $Ca^{+2}$ release of up to 50% from the competent osteogenic cell. This effect is highly specific to the parameters of the electrical code of Mode 1. Thus this code influences one major step of ossification, i.e., the mineralization of a bone growth site. Similar tissue culture studies using Mode 2 code signals have demonstrated that this code is responsible for enhanced protein production from similar competent osteogenic cells. This latter effect is also highly specific to the parameters of the electrical code of Mode 2. In other words, this code affects certain metabolic processes for these types of cells such as those involved in calcium uptake or release from mitochondria as well as the synthesis of collagen, a basic structural protein of bone.

These studies show that the electrical codes of Mode 1 and Mode 2 elicit individual tissue and cellular responses, indicating that each code contains a highly specific informational content therein. Based upon these and other studies, it has been possible to utilize Mode 1 or Mode 2 signals or a particular combination of Mode 1 and Mode 2 signals to achieve a specific response required to enable the functional healing of a bone disorder. These electrical modes have been applied successfully to human and animal patients for non-healing fractions such as congenital pseudarthrosis and non-unions as well as fresh fractures. Successes achieved in the congenital pseudarthrosis cases are particularly noteworthy, since normally 80% of children thus afflicted require amputation, since conventional treatments such as bone grafting and internal fixation are unsuccessful.

While there have been many investigations in the past of the response of living tissues and/or cells to electrical signals, clinical results to date using prior techniques have not been uniformly successful or generally accepted within the appropriate professional community. Several reasons contribute to this state. First, it has not been realized heretofore that electrical signals of very specific informational content are required to achieve a specifically desired beneficial clinical effect on tissue and/or cells. Second, most of the prior techniques utilize implanted electrodes, which by virtue of unavoidable faradaic (electrolysis) effects are often more toxic than beneficial in the treated site. Furthermore, the cells and/or tissues are subjected to a highly uncontrolled current and/or voltage distribution, thereby comprising the ability of the cells to respond, should they do so, to the applied signal. The highly uncontrolled current and/or voltage distribution also applies in the case of capacitatively coupled signals.

In contrast, the surgically non-invasive direct inductive coupling of electrical informational content of specific electrical codes as involved in the present invention produces within living tissue and/or cells a controlled response.

In brief, the present invention involves the recognition that the growth, repair and maintenance behavior of living tissues and/or cells can be modified beneficially by the application thereto of specific electrical information. This is achieved by applying pulse waveforms of voltage and concomitant current of specific time-frequency-amplitude relations to tissue and/or cells by a surgically non-invasive means through use of a varying electromagnetic field which is inductively coupled through direct induction into or upon the tissue and/or cells under treatment. The information furnished to the cells and/or tissues by these signals is designed to influence the behavior of non-excitable cells such as those involved in tissue growth, repair, and maintenance. These growth, repair and maintenance phenomena are substantially different from those involved in excitable cellular activity (e.g. nerves, muscles, etc.), particularly with respect to the type of perturbation required. Thus, the voltages and concomitant currents impressed on the cells and/or tissues are at least three orders of magnitude lower than those required to affect cellular activities such as cardiac pacing, bladder control, etc.

The invention will be more completely understood by reference to the following detailed description:

BRIEF DESCRIPTION OF THE DRAWINGS

FIG. 1 is a simplified view showing the treatment of a bone in accordance with the invention.

FIG. 2 is a perspective view of the treatment unit shown in FIG. 1.

FIG. 3 is a view (from the rear) of the unit shown in FIG. 2, showing the positioning of a coil therein used for treatment purposes.

FIG. 4 is a block diagram of an electrical system for energizing the coil shown in FIG. 3 for Mode 1 treatment.

FIG. 5 is a block diagram of an electrical system for energizing the coil shown in FIG. 3 for Mode 2 treatment.

FIGS. 5a and 5b are pulse waveform diagrams for Mode 1 and Mode 2 treatments, respectively, showing presently referred pulses as induced in living tissues and cells.

FIG. 6 shows alternative forms of negative pulse portions for Mode 2 treatment.

DETAILED DESCRIPTION

Referring to FIGS. 1 to 3, the leg 10 of a person having a broken bone as indicated as at 12 is shown as representative of the application of the invention to the stimulation of bone growth for healing purposes. A treatment head 14 is positioned outside the skin of the person, and is strapped in place by use of a strap 16 (secured to head 14 by fasteners 16a) which may include velcro material 18 thereon so that the strap may be wrapped about the leg and about the treatment head to maintain the treatment head in position against the leg. The treatment head 14 may include a foam material 20 on the inside surface thereof for the purpose of cushioning and ventilating the treatment head against the leg. It will be noted that the treatment head 14 is generally curved on the interior surface thereof so that it conforms to the shape of the leg under treatment.

The treatment head 14 includes therein a coil 22 which may be of any suitable shape. As shown in FIG. 3 the coil 22 is generally rectangular in shape so as to define a "window" within the interior portion of the turns of the coil. The coil 22 may lie in a plane or it may generally be curved to conform to the curvature of the treatment head 14. The coil 22 includes terminals 24 which extend away from the treatment head 14 to be coupled to a cable 26 for connection to a suitable energizing circuit, as will be explained below in more detail. A diode 27 may be included within the cable 26 for connection across the coil 22, as will also be explained below.

The treatment head 14 is positioned on the patient so that the "window" formed by the coil 22 is adjacent the break 12, i.e., adjacent the tissue under treatment. The coil 22 is energized, as will be explained in more detail below, and induces an electrical potential within the tissue under treatment. It has been found that a particular type of signal should be induced within the tissue and this is achieved by energizing the coil 22 by a circuit such as shown in FIG. 4 or FIG. 5 to produce the pulse signal shown in FIG. 5a or FIG. 5b.

Referring to FIG. 4, a variable dc supply 30 is coupled through a gate 32 to the treatment coil 22 (or coils as the case may be and as will be explained in more detail below). The gate 32 is under the control of control units 34 and 36 which cause a pulse signal consisting of repetitive pulses of electrical potential to be applied to the treatment coil 22. Each pulse, as shown in FIG. 5a, is composed of a "positive" pulse portion P1 followed by "negative" pulse portion P2 because of the stored electrical energy within the treatment coil. In the circuit of FIG. 4, a diode clamping unit 38 may be employed to limit the peak potential of that negative pulse portion. The diode clamping unit 38 may be one or more diodes connected across the coil 22, and may be advantageously located within the cable 26. The diode 27 shown in FIG. 1 constitutes such a clamping unit 38.

In FIG. 5a, the signals at the treatment coil 22 and hence the induced signal within the tissue to be treated are shown. At time $t1$, it is assumed that gate 32 is gated on by an appropriate signal from control unit 36 (designated a pulse width control unit) so that the electrical potential across the treatment coil 22 is raised from about zero volts along pulse segment 39 to a potential designated $v1$ in FIG. 5a. The signal across the treatment coil decays in a second pulse segment along the portion of the curve designated 40 in FIG. 5a. The slope of that curve is determined by the L/R time constant of the circuit of FIG. 4, i.e., the inductance of the treatment coil and the effective resistance of the circuit, including distributed factors of capacitance, inductance and resistance. For treatment of many tissues and cells, it is believed desirable to adjust the circuit parameters so that the portion 40 of the curve is as flat as possible, rendering the signal applied to the treatment coil 22 as rectangular in shape as possible. At the time $t2$, the gate 32 is gated off by the control unit 36. Just prior to being gated off, the signal across the treatment coil is at the potential $v2$ shown in FIG. 5a. The potential across the treatment coil drops from the level $v2$ in a third pulse segment 41 to a potential of opposite polarity designated $v3$ in FIG. 5a. The magnitude of the opposite polarity potential $v3$ may be limited by the diode clamping unit 38 to a relatively small value as compared with value $v1$. The signal across the treatment coil 22 then decays from the potential level $v3$ to the zero or reference potential level, finally effectively reaching that level at time $t3$. A predetermined period passes before the pulse repetition rate control unit 34 generates an appropriate timing signal to trigger the control unit 36 to generate a signal to turn gate 32 on again to continue the cycle just explained.

The control units may typically be monostable multivibrators, e.g., to generate appropriate timing signals and which may be variable to control pulse duration and repetition rate within desired limits. Further, the use of a variable dc supply 30 permits variation of the amplitude of the pulse signal as desired.

When pulse train operation (Mode 2) is employed, additional timing circuitry similar to units 34 and 36 in FIG. 4 are employed to provide the burst segment width and the burst segment repetition rate. Referring to FIG. 5, control units 35 and 37 control gate 33 to produce a signal applied to coil(s) 22 of the waveform type as shown in FIG. 5b. The circuit is otherwise the same as in FIG. 4, except that diode clamping unit 38 is omitted to permit the large negative pulse portions as shown in FIG. 5b. The control units 35 and 37 determine the number of pulses in a burst and the time between successive bursts.

It has been found that the signal across the treatment coil 22, and hence the induced signal within the tissue under treatment, should satisfy certain criteria. These criteria will be specified with respect to the signal as induced in the tissue and/or cells under treatment. Such induced signal may be monitored, if desired, by use of an auxiliary monitoring pickup coil (not shown) which is positioned at a distance from the treatment coil 22 corresponding to the distance of the tissue under treatment from that coil, as will be explained in more detail below. In any event, it has been found that the following criteria should be satisfied for effective treatment of living tissues and cells, in particular, hard tissue such as bone.

In the following presentation the signals shown in FIGS. 5a and 5b constitute the pulses of electrical potential and concomitant current generated by the coil and impressed upon the tissues and/or cells. These pulses have one polarity upon "energization" of the coil (termed herein the "positive" pulse portion and shown as the positive going portion of the waveform on FIGS. 5a and 5b). These pulses have an opposite polarity upon "de-energization" of the coil (termed herein the "negative" pulse portion and shown as the negative going portion of the waveform of FIGS. 5a and 5b). The terms "positive" and "negative" are intended to be relative only, as used herein, only for the purpose of indicating that pulse portions of opposite polarity, with respect to a reference potential level are involved.

It has been determined that the "positive" pulse portions should bear a predetermined relationship to the "negative" pulse portions in order to modify beneficially and with uniform results the behavior of living tissues and cells. This predetermined relationship has been achieved by the utilization of two different signal modes, as well as combination thereof.

In Mode 1 (see FIG. 5a), the asymmetrical waveform induced in tissue or cells by the alternate energization and de-energization of an electromagnetic coil is repeated at a frequency such that the overall duty cycle is no less than about 2%. This frequency, in mode 1, has typically been about 10–100 Hz with duty cycles of 20–30%. The basic relationship for mode 1 of the respective frequency amplitude content of the "positive" and "negative" pulse portions is as follows: pulse signal should be of a particular shape, namely, each "positive" pulse portion should be composed of at least three segments, e.g., the segments 39, 40 and 41 in FIG. 5a. As noted above, it has been found that a substantially rectangular shaped "positive" pulse signal portion is particularly useful in the treatment of tissue and cells, However, it is possible that other pulse configurations (other than a simple two-segment spike) may be useful. The peak amplitude of the final segment of each "positive" pulse portion, e.g., the potential $v_2$ in FIG. 5a should be no less than about 25% of the peak amplitude of the first segment 39 of the "positive" pulse portion, e.g., the potential $v_1$ in FIG. 5a.

The peak "negative" portion amplitude is denoted by $v_3$ in FIG. 5a. This peak amplitude should be no more than about ⅛ the peak amplitude of the "positive" pulse portion. The duration of each "positive" pulse portion (the time that elapses between times $t_1$ and $t_2$ in FIG. 5a) should be no longer than about 1/9 the time duration of the following "negative" pulse portion (the time elapsing between times $t_2$ and $t_3$ in FIG. 5a). Because the treatment system utilizes an electromagnetic coil, the energy of each "positive" pulse portion is equal to the energy of each "negative" pulse portion, i.e., the area in FIG. 5a embraced by the "positive" pulse portions is equal to the area embraced by the "negative" pulse portions. By satisfying the criteria just mentioned, the energy of each "negative" pulse portion is dissipated over a relatively long period of time, and the average amplitude of that negative pulse portion is limited. It has been found that such average negative amplitude should be no greater than about 1/6 the average amplitude of the "positive" pulse portion.

These relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has been found that the average magnitude of the "positive" pulse portion peak potential should be within the range of about 0.0001 to 0.01 volt per centimeter of tissue or cells, corresponding to between about 0.1 and 10 microampere per square centimeter of treated tissue and/or cells (based upon typical cell and tissue resistivities). It has been found that higher or lower pulse potentials will not result in a beneficial effect. It has also been found that the duration of each "positive" pulse portion (the time elapsed between times $t_1$ and $t_2$ in FIG. 5a) should be at least about 200 microseconds. If the time duration of each "positive" pulse portion is less than about 200 microseconds, the tissues and cells are not stimulated sufficiently to modify the repair or other processes. From a practical standpoint, the "positive" pulse portion duration should not be greater than about 1 millisecond. It has also been found that the repetition rate of the pulses should be within the range of about 65 to 75 Hz for bone and other hard tissues. Pulse treatments within this range have been found to be particularly effective with reproducible results for tissues and cells of this type. In general, however, pulse repetition rate should be between about 10 and 100 Hz for good results in tissues and cells.

For the treatment of bone disorders, and particularly for the treatment of pseudarthrosis, it has been found that for mode 1 an optimum induced "positive" pulse signal portion having a peak amplitude of between about 1 and 3 millivolts per centimeter of treated tissue (1 to 3 microamperes per square centimeter of treated tissue and/or cells) with the duration of each "positive" pulse portion being about 300 microseconds and the duration of each of the "negative" pulse portions about 3300 microseconds, and a pulse repetition rate of about 72 Hz represents a presently preferred and optimum induced pulse treatment as long as the pulse shape requirements noted above are met. Total treatment times may vary. It is presently believed that pulse signal treatments for periods each lasting for at least about 15 minutes, with one or more periods of treatment during a prescribed number of days may be effective in stimulating tissue and cell behavior. A preferred treatment regime using mode 1 has been found to be a minimum of 8 hrs/day for a period of 4 months in difficult cases and two weeks in less difficult cases.

In Mode 2 treatment (FIG. 5b), the asymmetrical waveforms induced in tissue or cells by the alternate energization and de-energization of an electromagnetic coil is applied in a pulse train modality, which contains bursts (pulse groups) of asymmetrical waveforms. Each burst of asymmetrical pulses has a duration such that the duty cycle of the burst portion is no less than about 1%. The burst frequency has typically been about from 5–50 Hz.

The basic relationships for Mode 2 of the respective frequency-amplitude content of the "positive" and "negative" pulses within the burst section of the pulse train are as follows: each "positive" pulse portion should be composed of at least three segments, e.g., the segments 39', 40' and 41' in FIG. 5b. For this mode, it has also been found that a substantially rectangular shaped "positive" pulse signal portion is particularly useful in the treatment of tissues and cells. However, it is possible that other pulse configurations other than a simple two segment spike may be useful. The peak amplitude of the final segment of each "positive" pulse portion, e.g., the potential $v_2$ in FIG. 5b should be no less than about 25% of the peak amplitude of the first segment 39 of the "positive" pulse portion, e.g., the potential $v_1$ in FIG. 5b.

The peak "negative" amplitude is denoted by $v_3$ in FIG. 5b. This "negative" peak amplitude should be no more than about 40 times the "positive" peak amplitude (in this case $v1$). This requirement may be met by utilizing "negative" pulse portions having several different waveshape forms, e.g., substantially rectangular, trapezoidal with exponential decay, bell shaped, or single spike with exponential decay as in representative waveforms a, b, c and d in FIG. 6.

The duration of each "positive" pulse portion (the time elapses between times t1 and t2 in FIG. 5b) should be at least about 4 times the duration of the following "negative" pulse portion (the time that elapses between times t2 and t3 in FIG. 5b). As noted above, since the treatment system utilizes an electromagnetic coil, the energy of each "positive" pulse portion is equal to the energy of each "negative" pulse portion, i.e., the area in FIG. 5b embraced by the "positive" pulse portions is equal to the area embraced by the "negative" pulse portions.

The pulse repetition rate of the pulses within the burst segment of the Mode 2 pulse train (the time elapsing between times t1 and t4) can be between about 2000 Hz and 10,000 Hz.

The width of the burst segment of the pulse train (the time elapsed between t1 and t5) should be at least about 1% of the time elapsed between t1 and t6.

By satisfying the criteria just mentioned, these relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has also been found that the average magnitude of the "positive" peak potential should be within the range of about 0.00001 to 0.01 volts per centimeter of tissues and/or cells (between about 0.01 and 10 microampere per square centimeter of treated tissue and/or cells).

It has been found that higher or lower pulse potentials will not result in a beneficial effect on tissues and/or cells. It has also been found that the duration of each "positive" pulse portion in the burst segment of the pulse train (i.e., the time elaspsed between t1 and t2 in FIG. 5b) should be at least about 1000 microseconds. It has also been found that the repetition rate of the burst segment should be within the range of about 5–15 Hz for bone and other hard tissues.

Each negative pulse portion within the burst segment of the pulse train should be of a duration no greater than about 50 microseconds and of an average amplitude no greater than about 50mv/cm of treated tissue and/or cells (about 50microamperes per square centimeter of treated tissue and/or cells).

For the treatment of bone disorders and particularly, for the treatment of pseudarthroses and non-unions, it has been found that an optimum induced "positive" pulse signal portion having a peak amplitude of between about 1 and 3 millivolts/centimeter of treated tissue (i.e., 1 to 3 microamperes per square centimeter of treated tissue and/or cells), with the duration of each "positive" pulse portion being about 200 microseconds and the duration of each of the "negative" pulse portions being about 30 microseconds and a time elaspsed between times t3 and t4 of FIG. 5b of 10 microseconds, and a pulse repetition rate of about 4000 Hz, and a burst segment width of about 5 milliseconds and a burst repetition rate of about 10 Hz represents a presently preferred and optimum induced pulse treatment in bone for Mode 2, as long as the pulse requirements noted above are met.

It is also believed that a single asymmetrical pulse as described in the burst segment of Mode 2 can be employed at a repetition rate similar to that used in Mode 1 for beneficial modification of tissue growth and repair.

Treatment of living tissues and cells by the above methods herein, in particular for hard tissue such as bone, has demonstrated an increased repair response and generally uniform results have been attained throughout all patient and animal treatments. Particularly beneficial results have been obtained in the cases of treatment of pseudarthrosis in which a bone union has been achieved following previous unsuccessful attempts by other treatment methods and in which amputation has been discussed as a possible alternative to regain function.

In practice, it is believed desirable to utilize as large a coil "window" as possible and to position the coil such that an adequate flux density is impressed upon the tissue and/or cells being treated. As is known, a time varying magnetic field induces a time varying voltage field orthogonal to it. That is, the geometry of the magnetic field lines determines the geometry of the induced voltage field. Because a relatively uniform induced voltage field is desired, the geometry of the magnetic field lines should be as uniform as possible, which may be achieved by rendering the size of the coil relatively large with respect to the area under treatment. At this particular time, it is not believed that there need be a particular orientation between the magnetic field lines and the tissue and/or cells being treated.

It is believed that the uniformity of the induced voltage field possible through electromagnetic treatment is responsible in many respects for the good treatment results which have been obtained, in distinction to the non-uniform fields which may and probably do result with other types of treatments, for example, utilizing electrostatic fields or by the creation of a potential gradient through the use of electrodes implanted within or on tissues or cells. In particular, an induced voltage field is present in a vacuum as well as in a conducting medium or an insulator. The field characteristics will in general be the same (within one percent) in these three cases, except in the case for which an induced current flow is sufficiently great to create a back electromotive force to distort the magnetic field lines. This condition occurs when the conducting medium has a high conductivity, e.g., a metal, and is large enough to intercept a substantial number of magnetic field lines. Living systems, i.e., tissue and/or cells, are much less of a conductor than a typical metal (general by at least $10^5$ orders of magnitude). Because of these considerations, the geometry of the magnetic field present in tissue and/or cells is undisturbed and remains unchanged as the tissue and/or cell growth process continues. Thus, with non-invasive electromagnetic treatment, it is believed that the potential gradient that is produced within the tissue and/or cells is constant regardless of the stage or condition of the treatment.

Such uniformity of induced potential is virtually impossible to be achieved through the use of implanted electrodes or by electrostatic coupling or by transformer coupled to electrodes, or by implanted coils coupled to electrodes. Since these latter types of treatments are dependent upon conductivity, which will vary within tissue and/or cells, the induced potential gradient will not be constant as the condition of the tissue and/or cells changes. Additionally, at any particular time within tissue and/or cells, individual localities of the material being treated will have different conductivity characteristics, which will result in differing potential gradients throughout the material treated.

For these reasons it is believed that a surgically non-invasive electromagnetic treatment of tissue and/or cells is greatly preferable to electrical treatment by other means.

Regarding typical coil parameters, it is believed that for typical bone breaks, coil windows of about 2.0 × 2.75 inches (for an adult) and 2 × 1.5 inches (for a child) are suitable. The wire employed in the coils may be B&S gauge 12 copper wire that is varnish coated to insulate the turns one from another. Coils of about 60 turns for an adult and 70 turns for a child seem to be suitable. For treatments in the oral cavity, coil sizes would be correspondingly smaller.

It is believed that the inductance of the treatment coil should be between about 1–5000 microhenries, and preferably between about 1000 and 3000 microhenries, with sufficiently low resistance (e.g., $10^{-3}$ to $10^{-1}$ ohms) and a high input coil driving signal between about 2 and 30 volts to induce the appropriate pulse potential in the tissue and/or cells treated. The lesser the inductance of the treatment coil, the steeper the slope of the curve 40 and 40' as shown in FIGS. 5a and 5b; the greater the inductance the flatter or more rectangular is the "positive" pulse that is produced.

The monitoring of the induced potential may be by actual electrodes making contact with the tissue and/or cells being treated or by use of a pickup coil positioned adjacent to the treatment coil 22 at a distance corresponding to the distance of the material under treatment from the coil. A typical pickup coil that has been employed is circular, about one-half centimeter in diameter, with about 67 or 68 turns of wire. The potential developed by the coil is divided by the length of the wire (in centimeters) to provide an induced voltage per centimeter number that is the same as the volts per centimeter induced in the tissue and/or cells under treatment.

A typical treatment utilizing a coil having a "window" 2 × 2.75 inches and 60 turns of number 17 gauge wire, including a diode at the coil such as the diode 27 in FIG. 3, produced the following induced voltages in a pickup coil, translated into millivolts per centimeter of tissue, for the pulse times (in microseconds) as follows (voltages and times are with reference to the waveform of FIG. 5):

| Induced Voltage | v1 | v2 | v3 | t1–t2 | t2–t3 |
|---|---|---|---|---|---|
| Maximum (at face of treatment coil) | 22 | 17 | 3.7 | 300 | 4200 |
| ⅝" from face of treatment coil | 15 | 11.5 | 2.5 | 300 | 4200 |
| 1¼" from face of treatment coil | 6.0 | 4.2 | 1.0 | 300 | 4200 |

The use of pulsing electromagnetic fields to control bone formation in a variety of conditions, now, is on a sound experimental and clinical basis. Thus, far, the development have had application in treating successfully congenital and acquired pseudarthrosis and fresh fractures in humans, increasing the rate of fracture and reactive periostitis repair in animals, and reducing bone loss in disuses osteoporosis of long bones. Success with the method hinges on the discovery of pulse patterns with specific time-frequency-amplitude relationships as outlined above.

EXAMPLES

In order to demonstrate efficacy the utilization of direct inductive coupling of electromagnetically induced pulsing voltages and concomitant current via modes 1 and 2 and combinations thereof for hard tissue growth and repair was initially applied in cases of congenital and acquired pseudarthrosis. In a group of patients only individuals who had been treated previously by one or more unsuccessful surgical attempts (grafting, internal fixation) were accepted. For most of these patients, amputation had been recommended by at least one qualified orthopedist. Throughout this study the necessity for pulse specificity was illustrated again and again. For example, when lack of ossification was the primary problem (usually the case for congenital pseudarthroses) mode 1 treatment was utilized with final functional bony union occurring only when the parameters of the pulse corresponded to those given above. On the other hand, when lack of bony matrix was the primary problem, mode 2 treatment was employed in order to achieve the production of collagen which is the primary supporting protein in bone structure. Since protein production and ossification are two completely different steps in bone formation, the highly selective nature of each of the signals utilized in modes 1 and 2 could be synergistically combined when neither matrix production or ossification were present in a given patient's treatment history. Thus, a combination of modes 1 and 2 was utilized with benefit in this type of situation.

In the case of congenital pseudarthroses the typical patient is between 1 and 10 years of age. The afflicted part is normally the distal tibia of one extremity. The patients are presented with an average of three prior unsuccessful surgical procedures and had the condition for an average of 5 years and all were candidates for amputation.

The treatment of such a patient was normally carried out using mode 1 treatment regime since the primary problem was due to a lack of ossification in the affected area.

The patient is prescribed the appropriate equipment by the attending orthopedic surgeon and carries out his treatment on an out-patient basis. Treatment time is typically 12 to 16 hours a day for about an average of 4 months.

Some 20 of this type of disorder have been treated to date with successful ossification achieved in approximately 90% of the treated individuals.

For acquired pseudarthrosis, ether traumatic or operative, patients are mostly adults and had an average number of three failed operations and an average of 2.5 years from onset of non-union. Amputation had been discussed for seventy percent of these individuals. Since in some cases the primary problem was lack of bony matrix typically visible radiographically as gaps in the bone of more than 2 mm in the fracture site, such a patient was treated commencing with mode 2 modality. When it was thought that sufficient non-ossified bony matrix was present mode 1 modality was employed to gain rapid immobilization of the fracture site.

Because of the particular pathology of several patients in this group, a combination of modes 1 and 2 was employed with this treatment being specifically mode 2 followed by mode 1. As in the case of congenital pseudarthrosis, the proper equipment was prescribed by the attending orthopedic surgeon and treatment was performed on an out-patient basis. Treatment time is typically 10–14 hours/day for periods ranging from 3 to 9 months.

Some 30 of this type of disorder have been treated to date with successful bony union observed in 75% of the treated individuals.

These clinical results clearly demonstrate that once the particular pathology of a bone disorder is diagnosed it can be selectively beneficially treated by the application of properly encoded changes in electrical environment.

Similar findings have been obtained from a study of bilateral fermoral and radial osteotomies in 160 rats. These animals were divided into two major groups; field exposed and control for an interval of 14 days after operation. Following sacrifice, the extent of fracture repair was judged on the basis of X-ray and histologic evaluation, coupled with non-destructive mechanical testing. These animal models were employed to evaluate the effectiveness of treatment modalities of Modes 1 and 2 and combinations thereof. Generally, when the osteotomy gap was less than 0.1 mm, a Mode 1 signal was effective since very little bony matrix was required for solidification. On the other hand, for wider osteotomies, substantially increased matrix production was observed over control animals when Mode 2 was employed. A combination of Modes 1 and 2 was employed in the latter case to obtain a stiffer repair site for an equivalent treatment time.

This was further evaluated by the response of these bones to mechanical testing. This was performed by subjecting the bone of the rats following sacrifice to cantilever loading at various deformations in accordance with the testing procedures described in "Acceleration of Fracture Repair By Electromagnetic Fields. A Surgically Non-invasive Method" by C. A. L. Bassett, R. J. Pawluk and A. A. Pilla published on pp. 242-262 of the *Annals of The New York Academy of Sciences* referenced above. The specimens were deformed in the antero-posterior, lateral-medial, postero-anterior, medial-lateral and again the antero-posterior positions.

The average response of a femur to this test at a deformation of 0.05 inch is shown in Table I as follows:

Table I

| Mechanical Load Values in Electrical Stimulation of Artificial Osteotomies in Adult Female Rat Femur | |
|---|---|
| Stimulation | Load at 0.05 in. Deformation |
| Control (untreated) | 42 gms. ± 5.2 gms. |
| Mode 1 Signal Figure 5a | 580 gms. ± 65 gms. |

In addition to radiographic and mechanical evidence of the effectiveness of the signal employed, histologic evidence further attests to this effectiveness.

Hemotoxylin and eosin stained longitudinal specimens show a much higher degree of maturation for the Mode 1 signal than in the control case.

For wider osteotomy gaps, treatment times of fourteen days showed that the active animals had a significantly larger callus than controls. Histologic evidence shows that the increase is at least 150% over controls.

Limited tooth extraction studies have been performed and show that pulses of the Mode 1 type may have a highly beneficial effect on the rate of healing and on bone loss in the oral cavity. The latter effect in the oral cavity is particularly important for the maintenance of mandibular and maxillar crestal bone height, a very important factor for implant fixation.

These observations all point to the fact that electromagnetic fields with highly specific pulse characteristics can be non-invasively inductively coupled to biological systems to control cell behavior. In the initial application of these principles, effects on bone cells have been investigated. Other biological processes, however, may eventually be proven to be controlled by similar techniques, e.g. malignancy, neuro-repair, inflammatory processes and immune response, among others.

In summary, it is believed that a unique electromagnetic and surgically non-invasive treatment technique has been discovered. Induced pulse characteristics appear to be highly significant, especially those relating to the time-frequency-amplitude relationships of the entire pulse or pulse sequence. It is believed that selection of particular time-frequency-amplitude relationships may be the key to successful treatments of varying cellular behavior in a variety of tissues.

It will be appreciated that the methods and apparatus described above are susceptible of modification. For example, while FIGS. 1 and 2 illustrate a treatment unit which may be strapped to the leg, treatment units incorporated in casts, e.g., may be employed. Further, treatment may be carried out by use of one or more coils of varying shapes positioned adjacent to tissue and/or cells to be treated. In fact, some treatments of humans have involved coils positioned upon opposite sides of a bone break. Coils with metal cores may also be used. In the case of treatment within the oral cavity, it is believed that double coils are advantageous, positioned, for example, on opposite sides of a tooth socket to stimulate repair of that socket.

Throughout the specification for Mode 1, a preferred pulse repetition rate of between about 65 and 75 hertz has been specified for bone and other hard tissue. The exact limits of the pulse repetition rate are not known for all types of tissues and cells. It is believed that preferred operating ranges will vary depending on the tissue and cell type. Positive results have been obtained, for example, in soft tissue treatment at 20 hertz.

Thus, the following claims should be taken to define the invention.

What is claimed is:

1. A surgically non-invasive method of treating living tissues and/or cells comprising electromagnetically inducing voltage and concomitant current pulses of a specific frequency-amplitude relation within said tissue and/or cells, wherein said pulses satisfy the following criteria:
    (a) each pulse is composed of a positive pulse-signal portion followed by a negative pulse-signal portion;
    (b) each positive pulse signal portion is composed of at least three segments, of which the peak amplitude of the final segment is no less than about 25 percent of the peak amplitude of the first segment;
    (c) the duration of each positive pulse signal portion is between about 200 microseconds and 1 millisecond, and is no longer than about 1/9 the duration of the following one of the negative pulse signal portions;
    (d) the repetition rate of the pulses is between about 10 and 100 Hz;
    (e) each positive pulse signal portion has an average amplitude of between about 0.0001 and 0.01 volts per centimeter of treated tissue and/or cells corresponding to between about 0.1 and 10 microamperes per square centimeter of treated tissue and/or cells;
    (f) each negative pulse signal portion has an average amplitude no greater than about 1/6 the average amplitude of each positive pulse signal portion;
    (g) each negative pulse signal portion has a peak amplitude from which it exponentially decays to about a zero reference level, and said negative pulse signal portion peak amplitude is no greater than about ½ the peak amplitude of said positive pulse signal portion.

2. The method of claim 1 in which said pulses occur at a pulse repetition rate of between about 65 and 75 Hz.

3. The method of claim 1 in which said positive pulse signal portions are substantially rectangular in shape.

4. The method of claim 1 in which said pulses are inductively induced by non-invasive means within said tissue and/or cells for one or more periods during a predescribed number of days, each period lasting for at least about 15 minutes.

5. The method of claim 1 in which the average amplitude of each negative pulse signal portion is between about 0.16 and 0.5 millivolts per centimeter of treated tissue and/or cells, corresponding to between about 0.16 and 0.5 microamperes per square centimeter of treated tissue and/or cells, and in which the average amplitude of each positive pulse signal portion is between about 1 and 3 millivolts per centimeter of treated tissue and/or cells, corresponding to between about 1 and 3 microamperes per square centimeter of treated tissue and/or cells.

6. The method of claim 5 in which the duration of each of said positive pulse signal portions is at least about 300 microseconds, and the duration of each of said negative pulse signal portions is at least about 3000 microseconds.

7. The method of claim 1 in which the duration of each of said positive signal portions is no more than about 1/12 the duration of the following one of said negative pulse signal portions.

8. The method of claim 1 applied to human hard tissue.

9. The method of claim 1 applied to a human oral cavity.

10. The method of claim 1 applied to human bone.

11. The method of claim 1 applied to non-human animal hard tissue.

12. The method of claim 1 applied to a non-human animal oral cavity.

13. The method of claim 1 applied to non-human animal bone.

14. The method of claim 1 including in combination therewith electromagnetically inducing an additional set of voltage and concomitant current pulses within said tissue and/or cells, wherein the waveform of said additional set of voltages and concomitant current pulses is a repetitive sequence of pulse groups, each pulse group including a series of asymmetrical pulses; each pulse of each pulse group comprises an initial positive-pulse portion and a succeeding negative-pulse portion, each positive-pulse portion being composed of at least three segments, the peak amplitude of the final segment being no less than about 10 per cent of the peak amplitude of the first segment, each negative-pulse portion having a peak amplitude no greater than about 40 times the peak amplitude of said positive-pulse portion, the duration of each positive-pulse portion being at least about 4 times the duration of the following negative-pulse portion, each negative-pulse portion having a duration no greater than about 50 microseconds, the frequency of the pulse portions within each pulse group being between about 2000 and 10000 Hz., and the duration of each pulse group being no less than about 1/100 and no more than ½ of the duration of the time between successive pulse groups.

15. The method of claim 14 in which said first mentioned voltage and concomitant current pulses and said additional set of pulses are sequentially applied to said tissue and/or cells.

16. The method of claim 15, in which the sequential application comprises one or more pulses of said first mentioned voltage and concomitant current pulses in sequential interlace with one or more pulse groups of said additional set of pulses.

17. The method of claim 14, in which said first mentioned voltage and concomitant current pulses and said additional set of pulses are concurrently applied to said tissue and/or cells.

18. The method of claim 1, in which each said pulse in a given repetition period is one of a group of successive and like pulses, said repetition rate applying to the recurrence frequency of said groups.

19. The method of claim 1, in which the step of subjecting tissue and/or cells to electromagnetic induction involves selection of two electrical treatment coils, placement of said coils on opposite sides of the tissue and/or cell region to be treated, and exciting said coils in flux-aiding polarity and phase.

20. A surgically non-invasive method of treating living tissue and/or cells comprising subjecting said tissue and/or cells by electromagnetic induction to voltage and concomitant current pulses therewithin, wherein the waveform of said voltage and concomitant current pulses is a repetitive sequence of pulse groups, each pulse group comprising a plurality of asymmetrical positive and negative pulse portions; each positive portion comprising at least three segments, wherein:
  (a) the peak amplitude of the final segment is no less than about 10 per cent of the peak amplitude of the first segment,
  (b) each negative pulse portion has a peak amplitude no greater than about 40 times the peak amplitude of said positive pulse portion,
  (c) the duration of each positive pulse portion is at least about 4 times the duration of the following negative pulse portion,
  (d) each negative pulse portion has a duration no greater than about 50 microseconds,
  (e) the frequency of the pulse portions within each pulse group is between about 2000 and 10000 Hz., and
  (f) the duration of each pulse group is no less than about 1/100 and no more than about ½ of the duration of time between successive pulse groups.

21. The method of claim 20 in which each positive pulse portion within a pulse group persists for at least about 100 microseconds.

22. The method of claim 20 in which the pulse groups repeat at a frequency of between about 5 and 50 Hz.

23. The method of claim 20 in which the positive pulse portions in the pulse groups are each of an average potential of between about 0.00001 and 0.01 volts per centimeter of treated tissue and/or cells corresponding to between about 0.01 and 10 microamperes per square centimeter of treated tissue and/or cells.

24. The method of claim 20 in which said positive pulse portions each persist for at least about 100 microseconds and are each of an average potential of between about 0.00001 and 0.01 volts per centimeter of treated tissue and/or cells corresponding to between about 0.01 and 10 microamperes per square centimeter of treated tissue and/or cells, said negative pulse portions each persist for at least about 10 microseconds, and said pulse groups repeat at a frequency in the range between about 5 and 50 Hz.

25. The method of claim 24 in which the average amplitude of each positive pulse portion within each pulse group is between about 0.001 and 0.003 volts per centimeter of treated tissue and/or cells corresponding to between about 1 and 3 microamperes per square centimeter of treated tissue and/or cells, the duration of each of said positive pulse portions is at least about 200 microseconds and the duration of each of said negative pulse portions is less than about 40 microseconds, the duration of each combined positive and following negative pulse portion is no more than about 300 microseconds, and the repetition rate of the pulse groups is at least about 10 Hz.

26. The method of claim 20 in which said tissue and/or cells are treated for one or more periods during a prescribed number of days, each period lasting for at least about 15 minutes.

27. The method of claim 20 applied to human hard tissue.

28. The method of claim 20 applied to a human oral cavity.

29. The method of claim 20 applied to human bone.

30. The method of claim 20 applied to non-human animal hard tissue.

31. The method of claim 20 applied to a non-human animal oral cavity.

32. The method of claim 20 applied to non-human animal bone.

33. The method of claim 20, in which the step of subjecting tissue and/or cells to electromagnetic induction involves selection of two electrical treatment coils, placement of said coils on opposite sides of the tissue and/or cell region to be treated, and exciting said coils in flux-aiding polarity and phase.

34. A surgically non-invasive method of treating living tissue and/or cells comprising subjecting said tissue and/or cells by electromagnetic induction to voltage and cooncomitant current pulses therewithin, wherein the waveform of said voltage and concomitant current pulses is a repetitive sequence of individual pulses, each pulse comprising a plurality of asymmetrical positive and negative pulse portions; each positive portion comprising at least three segments, wherein:
  (a) the peak amplitude of the final segment is no less than about 10 per cent of the peak amplitude of the first segment,
  (b) each negative pulse portion has a peak amplitude no greater than about 40 times the peak amplitude of said positive pulse portion,
  (c) the duration of each positive pulse portion is at least about 4 times the duration of the following negative pulse portion,
  (d) each negative pulse portion has a duration no greater than about 50 microseconds, and
  (e) the frequency of the pulse portions is between about 10 and 100 Hz.

35. The method of claim 34 in which each said positive pulse portions persists for at least about 100 microseconds and is of an average potential of between about 0.00001 and 0.01 volts per centimeter of treated tissue and/or cells corresponding to between about 0.01 and 10 microamperes per square centimeter of treated tissue and/or cells, each said negative pulse portions persists for at least about 10 microseconds.

36. The method of claim 34, in which the average amplitude of each positive pulse portion is between about 0.001 and 0.003 volts per centimeter of treated tissue and/or cells corresponding to between about 1 and 3 microamperes per square centimeter of treated tissue and/or cells, the duration of each positive pulse portion is at least about 200 microseconds and the duration of each negative pulse portion is less than about 40 microseconds, the duration of each combined positive and following negative pulse portion is no more than about 300 microseconds.

37. The method of claim 34, in which the step of subjecting tissue and/or cells to electromagnetic induction involves selection of two electrical treatment coils, placement of said coils on opposite sides of the tissue and/or cell region to be treated, and exciting said coils in flux-aiding polarity and phase.

38. A surgically non-invasive method of treating living tissues and/or cells, comprising electromagnetically inducing quasi-rectangular asymmetrical voltage and concomitant current pulses of a specific frequency-amplitude relation within said tissue and/or cells, wherein said pulses satisfy the following criteria:
  (a) each pulse is composed of a pulse-signal portion of a first polarity and greater magnitude and lesser time duration, in alternation with a second pulse-signal portion of opposite polarity and lesser magnitude and greater time duration;

(b) the peak magnitude of said first-mentioned pulse-signal portions is no greater than about 40 times the peak magnitude of said second-mentioned pulse-signal portions;

(c) the time duration of each of said first-mentioned pulse-signal portions is no greater than about ¼ the time duration of an adjacent one of said second-mentioned pulse-signal portions;

(d) the repetition rate of said pulses is between about 10 ad 10000 Hz., and (e) each of said first-mentioned pulse-signal portions has an average amplitude of between about 0.0001 and 0.01 volts per centimeter of treated tissue and/or cells corresponding to between about 0.1 and 10 microamperes per square centimeter of treated tissue and/or cells.

39. The method of claim 38, in which each first-polarity pulse-signal portion is composed of at least three segments, of which the peak amplitude of the final segment is no less than about 25 percent of the peak amplitude of the first segment; the duration of each first-polarity pulse-signal portion is between about 200 microseconds and 1 millisecond, and is no longer than about 1/9 the duration of an adjacent one of the opposite-polarity pulse-signal portions; and the repetition rate of the pulses is between about 10 and 100 Hz.

40. The method of claim 38, in which the waveform of said voltage and concomitant current pulses is a repetitive sequence of discrete pulse groups, each pulse group comprising a plurality of said first and second pulse-signal portions, the duration of each pulse group being no less than about 1/100 and no more than about ½ of the time duration between successive pulse groups.

41. The method of claim 38, in which each first-mentioned pulse-signal portion has a duration no greater than about 50 microseconds, and the frequency of the pulses is between about 10 and 100 Hz.

42. A surgically non-invasive method of altering the behavior of living cells and/or tissues, said method comprising subjecting said living cells and/or tissue to the electromagnetic induction of a generally rectangular electrochemical information signal which controllably modifies fundamental cellular processes involved in growth, repair and maintenance when applied in predetermined time and informational sequence, said electrochemical informational signal being contained in a waveform having within said cells and/or tissues the following electrical parameters:

(a) said waveform comprising multi-segment voltage and concomitant current pulses each of which is composed of a pulse-signal portion of one polarity and greater magnitude and lesser time duration, alternating with an adjacent pulse-signal portion of opposite polarity and lesser magnitude and greater time duration;

(b) the peak magnitude of one of said pulse-signal portions being no greater than about 40 times the peak magnitude of an adjacent pulse-signal portion;

(c) the time duration of said one of said pulse-signal portions being no greater than about ¼ the time duration of the adjacent pulse-signal portion;

(d) the repetition rate of said pulse-signal portions being between about 10 and 10000 Hz.; and (e) said one of said pulse-signal portions having an average amplitude of between about 0.0001 and 0.01 volts/cm of treated tissue and/or cells, corresponding to between about 0.1 and 10 microamperes/square centimeter of treated tissue and/or cells.

43. A surgically non-invasive method of altering the behavior of living cells and/or tissues, said method comprising subjecting said living cells and/or tissues to the electromagnetic induction of generally rectangular electrochemical informational signals which controllably modify fundamental cellular processes involved in growth, repair and maintenance when applied in predetermined time and informational sequence, said signals each comprising at least two asymmetrical pulse-signal portions of different polarity and amplitude and time, asymmetry of said pulse-signal portions being both as to amplitude and time and to an extent of at least about 4:1, the minimum time duration of one of said pulse-signal portions being no greater than about 50 microseconds, and the minimum average magnitude of the other of said pulse-signal portions being at least about 0.00001 volts per centimeter of tissues and/or cells corresponding to at least about 0.01 microampere per square centimeter of treated tissue and/or cells.

44. Apparatus for electromagnetically treating living tissue and/or cells, comprising coil means adapted to be positioned in therapeutically beneficial proximity to the tissue and/or cells to be treated, pulse generator means connected to said coil means for exciting the same with a repetitive voltage pulse, whereby said coil means may create a varying electromagnetic field within said tissue and/or cells to thereby induce within said tissue and/or cells repetitive therapeutic pulses of electrical energy that satisfy the following criteria:

(a) each therapeutic pulse is composed of positive pulse-signal portion followed by a negative pulse-signal portion;

(b) each positive pulse-signal portion is composed of at least three segments, of which the peak amplitude of the final segment is no less than about 25 percent of the peak amplitude of the first segment;

(c) the duration of each positive pulse-signal portion is between about 200 microseconds and 1 millisecond, and is no longer than about 1/9 the duration of the following one of the negative pulse-signal portions;

(c) the repetition rate of the pulses is between about 10 and 100 Hz.;

(e) each positive pulse-signal portion has an average amplitude of between about 0.001 and 0.01 volts per centimeter of treated tissue and/or cells corresponding to between about 0.1 and 10 microamperes per square centimeter of treated tissue and/or cells;

(f) each negative pulse-signal portion has an average amplitude no greater than about 1/6 the average amplitude of each positive pulse-signal portion;

(g) each negative pulse-signal portion has a peak amplitude from which it exponentially decays to about a zero reference level, and said negative pulse-signal portion peak amplitude is no greater than about ⅓ the peak amplitude of said positive pulse-signal portion.

45. Apparatus for electromagnetically treating living tissue and/or cells, comprising coil means adapted to be position in therapeutically beneificial proximity to the tissue and/or cells to be treated, pulse-generator means connected to said coil means for exciting the same with a repetitive sequence of electrical pulses, whereby said coil means may create a varying electromagnetic field within said tissue and/or cells to thereby induce within said tissue and/or cells a repetitive sequence of therapeutic pulse groups, each pulse group comprising a plurality of asymmetrical positive and negative pulse portions; each positive portion being composed of at least three segments, wherein:
  (a) the peak amplitude of the final segment is no less than about 10 per cent of the peak amplitude of the first segment,
  (b) each negative pulse portion has a peak amplitude no greater than about 40 times the peak amplitude of said positive pulse portion,
  (c) the duration of each positive pulse portion is at least about 4 times the duration of the following negative pulse portion,
  (d) each negative pulse portion has a duration no greater than about 50 microseconds,
  (e) the frequency of the pulse portions within each pulse group is between about 2000 and 10000 Hz., and
  (f) the duration of each pulse group is no less than about 1/100 and no more than about ½ of the duration of time between successive pulse groups.

46. Apparatus for electromagnetically treating living tissue and/or cells, comprising coil means adapted to be positioned in therapeutically beneficial proximity to the tissue and/or cells to be treated, pulse-generator means connected to said coil means for exciting the same with a repetitive voltage pulse, whereby said coil means may create a varying electromagnetic field within said tissue and/or cells to thereby induce within said tissue and/or cells therapeutic pulses of electrical energy that satisfy the following criteria:
  (a) each therapeutic pulse comprises a plurality of asymmetrical positive and negative pulse portions;
  (b) each positive portion is composed of at least three segments;
  (c) the peak amplitude of the final segment is no less than about 10 per cent of the peak amplitude of the first segment;
  (d) each negative pulse portion has a peak amplitude no greater than about 40 times the peak amplitude of said positive pulse portion;
  (e) the duration of each positive pulse portion is at least about 4 times the duration of the following negative pulse portion,
  (f) each negative pulse portion has a duration no greater than about 50 microseconds, and
  (g) the frequency of the pulse portions is between about 10 and 100 Hz.

47. Apparatus for electromagnetically treating living tissue and/or cells, comprising coil means adapted to be positioned in therapeutically beneficial proximity to the tissue and/or cells to be treated, pulse-generator means connected to said coil means for exciting the same with a repetitive voltage pulse, whereby said coil means may create a varying electromagnetic field within said tissue and/or cells to thereby induce within said tissue and/or cells therapeutic pulses of electrical energy that satisfy the following criteria:
  (a) each pulse is composed of a pulse-signal portion of a first polarity and greater magnitude and lesser time duration, in alternation with a second pulse-signal portion of opposite polarity and lesser magnitude and greater time duration;
  (b) the peak magnitude of said first-mentioned pulse-signal portions is no greater than about 40 times the peak magnitude of said second-mentioned pulse-signal portions;
  (c) the time duration of each of said first-mentioned pulse-signal portions is no greater than about ¼ the time duration of an adjacent one of said second-mentioned pulse-signal portions;
  (d) the repetition rate of said pulses is between about 10 and 10000 Hz., and
  (e) each of said first-mentioned pulse-signal portions has an average amplitude of between about 0.0001 and 0.01 volts per centimeter of treated tissue and/or cells corresponding to between about 0.1 and 10 microamperes per square centimeter of treated tissue and/or cells.

48. Apparatus according to claim 47, in which said criteria are limited in the following respect: each first-polarity pulse-signal portion is composed of at least three segments, of which the peak amplitude of the final segment is no less than about 25 percent of the peak amplitude of the first segment; the duration of each first-polarity pulse-signal portion is between about 200 microseconds and 1 millisecond, and is no longer than about 1/9 the duration of an adjacent one of the opposite-polarity pulse-signal portions; and the repetition rate of the pulses is between about 10 and 100 Hz.

49. Apparatus according to claim 47, in which said criteria are limited in the following respect: the waveform of said voltage and concomitant current pulses is a repetitive sequence of discrete pulse groups, each pulse group comprising a plurality of said first and second pulse-signal portions, the duration of each pulse group being no less than about 1/100 and no more than about ½ of the time duration between successive pulse groups.

50. Apparatus according to claim 47, in which said criteria are limited in the following respect: each first-mentioned pulse-signal portion has a duration no greater than about 50 microseconds, and the frequency of the pulses is between about 10 and 100 Hz.

* * * * *